(12) United States Patent
Lenselink et al.

(10) Patent No.: US 6,645,932 B2
(45) Date of Patent: Nov. 11, 2003

(54) CHEMICAL COMPOUNDS AND PERFUME COMPOSITIONS

(75) Inventors: Willem Lenselink, Voorthuizen (NL); Anton Pieter J. van Manen, Putten (NL)

(73) Assignee: PFW Aroma Chemical B.V., Me Barneveld (NL)

( * ) Notice: Subject to any disclaimer, the term of this patent is extended or adjusted under 35 U.S.C. 154(b) by 0 days.

(21) Appl. No.: 10/005,754

(22) Filed: Oct. 29, 2001

(65) Prior Publication Data

US 2002/0160931 A1 Oct. 31, 2002

Related U.S. Application Data

(63) Continuation of application No. PCT/NL01/00637, filed on Aug. 29, 2001.

(30) Foreign Application Priority Data

Aug. 30, 2000 (EP) .......................................... 00203021

(51) Int. Cl.$^7$ .................................................. A61K 7/46
(52) U.S. Cl. .......................................................... 512/14
(58) Field of Search ............................. 512/1, 8, 14, 20, 512/25, 26, 27; 568/303, 308, 309, 325, 329, 330, 420, 425, 426, 445, 446

*Primary Examiner*—Jill Warden
*Assistant Examiner*—Monique T. Cole
(74) *Attorney, Agent, or Firm*—Hoffmann & Baron, LLP

(57) ABSTRACT

The invention relates to new chemical compounds useful as perfumes or as components of perfumes. More specifically it relates to alkyl-substituted 2-acylindenes and isomeric mixtures thereof, as well as to perfume compositions comprising said compounds. Furthermore, the invention relates to the use of said compounds and methods of making said compounds.

14 Claims, No Drawings

CHEMICAL COMPOUNDS AND PERFUME COMPOSITIONS

This application is a continuation of International Patent Application PCT/NL01/00637 filed on Aug. 29, 2001.

BACKGROUND OF THE INVENTION

The invention relates to new chemical compounds useful as perfumes or as components of perfumes. More specifically it relates to alkyl-substituted 2-acylindenes and isomeric mixtures thereof.

There is a continuing search for materials having useful perfumery fragrance characteristics. These materials are sought either as replacements for naturally occurring compounds or as totally new scents or odour notes in their own right. For practicability reasons such materials should possess other favorable properties e.g. substantivity and stability in applications, all in addition to their useful odour notes.

SUMMARY OF THE INVENTION

It is the object of the present invention to provide a series of novel and practicable synthetic materials or isomeric mixtures thereof, being alkyl-substituted indenes comprising an acyl moiety in the 2-position, and possessing very useful and strong odours with woody, straw- and hay-like notes. These novel indenes are represented by the generic Formula I

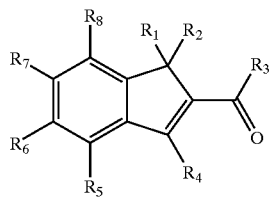

wherein $R_1$, $R_2$ each represent a lower alkyl group and $R_3$, $R_4$, $R_5$, $R_6$, $R_7$ and $R_8$ each represent hydrogen or a lower alkyl group or wherein two substituents chosen from $R_1$, $R_2$, $R_3$, $R_4$, $R_5$, $R_6$, $R_7$ or $R_8$ together may represent a di-, tri- or tetra- or pentamethylene moiety or a lower alkyl-substituted di-, tri- or tetra- or pentamethylene moiety and the remaining substituents represent hydrogen or a lower alkyl group, and wherein the total number of carbon atoms in formula I is twenty two or less, with the proviso that $R_1$ and $R_2$ together do not represent a tetramethylene moiety if $R_3$, $R_4$, $R_5$, $R_6$, $R_7$ and $R_8$ all represent hydrogen, and with the proviso that $R_8$ does not represent hydrogen if $R_1$, $R_2$, $R_4$, $R_5$, $R_6$, $R_7$ and $R_8$ all represent a methyl group.

In the present context the term "lower alkyl" indicates a straight or branched alkyl group or a cycloalkyl or alkyl-substituted cycloalkyl group, an of 1–6 carbon atoms.

It will be apparent that the novel indenes can exist in a variety of positional, stereoisomeric and enantiomeric forms and it is intended that these be included within the structural formulae.

In the compounds of the invention represented by the generic Formula I. $R_1$, $R_2$ each represent a lower alkyl group and $R_3$, $R_4$, $R_5$, $R_6$, $R_7$ and $R_8$ each represent hydrogen or a lower alkyl group, or two substituents chosen from $R_1$, $R_2$, $R_3$, $R_4$, $R_5$, $R_6$, $R_7$ or $R_8$ together may represent a di-, tri- or tetra- or pentamethylene moiety or a lower alkyl-substituted di-, tri- or tetra- or pentamethylene moiety and the remaining substituents represent hydrogen or a lower alkyl group, with the proviso that $R_1$ and $R_2$ together do not represent a tetramethylene moiety if $R_3$, $R_4$, $R_5$, $R_6$, $R_7$ and $R_8$ all represent hydrogen, and with the proviso that $R_3$ does not represent hydrogen if $R_1$, $R_2$, $R_4$, $R_5$, $R_6$, $R_7$ and $R_8$ all represent a methyl group.

In a preferred embodiment of the invention $R_3$ represents an alkyl group of four carbon atoms or less. In a more preferred embodiment $R_8$ is a methyl group. In an alternative embodiment $R_1$, $R_2$ are selected from methyl and ethyl groups and $R_4$, $R_5$, $R_6$, $R_7$ and $R_8$ each are selected from hydrogen, methyl and ethyl groups with a total number of carbon atoms in $R_1$, $R_2$, $R_3$, $R_4$, $R_5$, $R_6$, $R_7$ and $R_8$ together of eight or less. According to a specially preferred embodiment $R_1$, $R_2$ and $R_4$ represent each a methyl group.

DESCRIPTION OF THE PREFERRED EMBODIMENTS

The compounds of the invention are new. Only a few, simple alkyl-substituted 2-acylindenes are known, see for example Chem. Abstr. 114:121685; 105:115070; 93:238411; 107:175558; 90:54197; 84:121530; 83:131170; 117:131346; 110:94192; 109:54897; 107:217199; 107:40061; 105:226283; 95:23687; 79:136870 and 79:115338. These compounds appear to be mainly of scientific interest or are useful as intermediates for veterinary sedative antagonists or are rated odorless. None of them relates to possible uses as perfume or as component of perfumes.

In British patent application 2233645 the preparation and the use for the improvement of the fragrance of perfume compositions of 2-acylindanes are disclosed. Although these indanes are said to have no particularly powerful fragrance themselves, they would have an extra "harmonizing" and "rounding off" effect when added to other odoriferous materials in very low concentrations. The method of preparation of the disclosed indanes is mainly of academic interest and involves many laborious and impractical steps with low overall yields and would not be suitable for cost-effective industrial production.

For the chemist skilled in the art it will be apparent that the structural and three-dimensional conformation of the novel 2-acylindenes of the present invention differs significantly from the 2-acylindanes disclosed in British patent application 2233645. For the fragrance chemist skilled in the art it is understood that the three-dimensional position of the osmopheric group, being the ketone moiety of the acyl group, relative to the plain of the backbone of the molecule is decisive for the odour characteristic of the molecule. In 2-acylindanes the carbon atom in the 2-position is using four $sp^3$-hybridized orbitals to form tetrahedral bonds with the four atoms to which it is connected in a three-dimensional configuration. Consequently the position of the acyl moiety is out of the plain of the cyclic skeleton of the molecule. This is significantly different from the situation in 2-acylindenes of the present invention, wherein the carbon atom in the 2-position uses three $sp^2$-hybridized orbitals to form trigonal bonds with the three atoms to which it is connected, in a two-dimensional configuration. Therefor, in the case 2-acylindenes the position of the acyl moiety is in the plain of the cyclic skeleton of the molecule, which for fragrance chemists skilled in the art makes the odour characteristics unpredictable and unexpected over the prior art.

The novel indenes of the invention can be prepared by methods known to the art for analogous compounds e.g. as described in the literature references herein above. Of the methods known, the preferred method for each compound of the invention may be different and will depend on considerations of economics, availability of starting materials, byproduct formation, technical feasibility, safety, organoleptic grade produced, and the like, which parameters, circumstances and conditions may be subject to change over time, location, facility, etc.

A preferred chemical method in this context involves selective formylation or acylation of the alkene moiety of indenes of the generic Formula II,

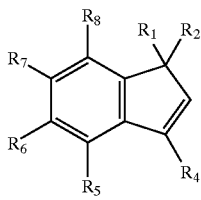

wherein the provisos for $R_1$, $R_2$, $R_4$, $R_5$, $R_6$, $R_7$ and $R_8$ are the same as defined herein above for Formula I, by general methods known to the art e.g. as set forth in J. March, Advanced Organic Chemistry: Reactions, Mechanisms and Structure, 4th edition, J. Wiley & Sons, N.Y., 1992, pp. 598–600, and references cited therein, and in G. A. Olah, Friedel Crafts and Related Reactions, Interscience Publishers, 1964, vol. III, part 2, pp. 1033–1071, and references cited therein. The starting indenes of Formula II can be prepared by methods known to the art e.g. as set forth in the references cited in CA 95:42765; CA 95:24598; CA 93:71383; CA 74:87684; CA 54:24584; CA 47:2169; CA 44:1056 and CA 43:5762.

An alternative preferred chemical method of preparation of the compounds of the invention involves conversion under Friedel Crafts acylation conditions, generally known to the art, e.g. as set forth in the references cited herein above, of indanes represented by the generic Formula III, wherein the provisos for $R_1$, $R_2$, $R_4$, $R_5$, $R_6$, $R_7$ and $R_8$ are the same as defined

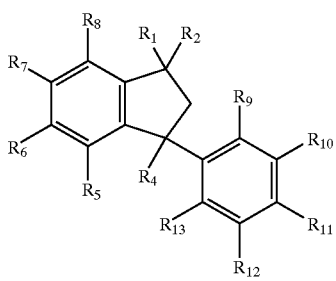

herein above for Formula I, and wherein $R_9$, $R_{10}$, $R_{11}$, $R_{12}$, and $R_{13}$ each represent hydrogen or a lower alkyl group or wherein two substituents chosen from $R_1$, $R_2$, $R_3$, $R_4$, $R_5$, $R_6$, $R_7$, $R_8$, $R_9$, $R_{10}$, $R_{11}$, $R_{12}$ or $R_{13}$ or together may represent a di-, tri- or tetra- or pentamethylene moiety or a lower alkyl-substituted di-, tri- or tetra- or pentamethylene moiety and the remaining substituents represent hydrogen or a lower alkyl group, and wherein the total number of carbon atoms in formula III is fifty or less. The indanes of Formula III can be prepared by methods known to the art e.g. as set forth in G. A. Olah, "Friedel Crafts and Related Reactions", Interscience Publishers, 1964, Vol. II, part 2, pp. 952–962 and the references cited therein The novel 2-acylindenes of the invention exhibit a variety of useful odour nuances with long-lasting, strong and diffusive, dry woody, straw- and hay-like notes with radiance and odour substantivity, which makes them specially suitable to be applied in fabric care, functional care and personal care consumer products. They bring a significant contribution to woody ambery fragrance combinations and as such add great depth to a fragrance combination even in very small quantities. They can be used as fragrances per se or as components of a fragrance composition. The term "fragrance composition" is used to denote a mixture of compounds including, for example, natural oils, synthetic oils, alcohols, aldehydes, ketone, esters, lactone, ethers, hydrocarbons, nitrites and other classes of chemical compounds which are admixed so that the combined odours of the individual components produce a pleasant or desired fragrance. Such fragrance compositions of the novel compounds of the invention alone can be used in conjunction with carriers, vehicles or solvents containing also as needed, dispersants, emulsifiers, surface-active agents, aerosols propellants, odour release influencing agents and the like. In fragrance compositions the individual components contribute to their particular olfactory characteristics, but the overall effect of the composition is the sum of the effect of each ingredient. Thus, the compounds of the invention can be used to alter, enhance, or reinforce the aroma characteristics of the other natural or synthetic materials making up the fragrance composition, for example, by highlighting or moderating the olfactory reaction contributed by another ingredient or combination of ingredients.

The amount of the compounds of the invention that will be effective, depends on many factors including the characteristics of the other ingredients, their amounts and the effects which are desired. It has been found that as little as 0.001% by weight of compounds of this invention can be used to alter the effect of a fragrance composition. The amount employed will depend on considerations of cost, nature of end product, the effect desired in the finished product, and the particular fragrance sought, but will usually not be more than about 40% by weight.

The compounds disclosed herein can be used in a wide variety of applications, by way of example but not limited thereto, detergents and soaps, fabric softeners, fabric care products, fabric sprays, fabric deodorants, ironing added products, dryer added product, optical whiteners, odour masking products, personal hygiene care products, air fresheners, perfumes, colognes, after shave lotions, preparations such as bath oils and bath salts, hair preparations such as lacquers, brilliantines, pomades and shampoos, cosmetic preparations such as creams, deodorants, hand lotions and sun screens, powders such as talcs, dusting powders, face powders, masking agents, household products such as bleaches, cleaners, dish washing products, scourers, toilet cleaners, carpet cleaners and in technical products such as paints, inks, shoe polish and automobile wax.

The following examples illustrate the invention without limitation thereto.

EXAMPLE 1

To a mixture of 20 g 1,3,3-trimethylindene (see e.g. J. Am. Chem. Soc. 76, 5430 (1954) ) 13 g acetyl chloride and 55 ml 1,2-dichloroethane in a nitrogen atmosphere was dosed with stirring 21.5 g aluminum trichloride over a period of one and a half hour and at a temperature of 20–25° C. After an additional stirring period of 30 minutes at 20° C. the mixture was poured on ice and stirred for another hour. The organic layer was washed with subsequently 5%-sodium carbonate solution, saturated sodium chloride solution and concentrated by means of a rotatory evaporator. Vacuum distillation of the residue yielded a 15.3 g of a fraction boiling up to 145° C. at 3 mm Hg. Recrystallization from methanol yielded 10 g 2-acetyl-1,3,3-trimethylindene of 99.8% purity, mp 104.5–105.0° C.

EXAMPLE 2

A mixture of about 1:1 by weight of 1,1,3,5-tetraraethylindene and 1,1,3,6 tetramethylindene (prepared from toluene and mesityloxide confirm the method set forth in Bull. Soc. Chim., 16, 181 (1949)) was acetylated analogous to Example 1, yielding after recrystallization from methanol 27.1% of an about 1:1 mixture of 2-acetyl-1,1,3,5-tetramethylindene and 2-acetyl-1,1,3,6-tetramethylindene bp 120–128° C. at 1.5 mm Hg, mp 97–98° C.

EXAMPLE 3

A mixture of about 9:1 weight of 1,1,3-trimethyl-5-t-butylindene and 1,1,3-trimethyl-6-t-butylindene (prepared from t-butylbenzene and mesityloxide conform the method set forth in Bull. Soc. Chim., 16, 181 (1949)) was acetylated analogous to Example 1. The fraction boiling from 100–140° C. at 1 mm Hg was recrystallized from methanol yielding 97.3% pure 2-acetyl-1,1,3,5-tetramethylindene.

EXAMPLE 4

To a mixture of 50.8 g 90.8% pure 1,1,2,5-tetramethyl-3-(4-methyl-benzyl)indane and 52.5 g 1,2-dichloroethane was added with stirring at 28–30° C. a mixture of 26.7 g aluminum trichloride, 14.8 g acetyl chloride and 75 g 1,2-dichloroethane in the course of one hour and twenty minutes. After an additional stirring period of 30 minutes at 20° C. the mixture was poured on ice and stirred for another hour. The organic layer was washed with subsequently 5%-sodium carbonate solution, saturated sodium chloride solution and concentrated by means of a rotatory evaporator yielding 34.9% 2-acetyl-1,1,3,5-tetramethylindene in 45.6 g residue. Recrystallization from methanol gave 99.4% pure 2-acetyl-1,1,3,5-tetramethylindene.

EXAMPLE 5

Perfume compositions, especially suited for use in cosmetic applications e.g. creams, were prepared by mixing the following ingredients:

|   |   | Parts by weight |
|---|---|---|
| A. | Frutalone (PFW) | 10 |
|   | Turboxan (PFW) | 40 |
|   | Cynthaflor (PFW) | 150 |
|   | Majantol (FR) | 150 |
|   | Dihydroisojasmonate (PFW) | 150 |
|   | α-Hexylcinnamic aldehyde | 150 |
|   | Citronellol 700 (BBA) | 340 |
|   | Dipropylene glycol | 10 |
|   |   | 1000 |

B. The formulation above wherein the 10 part by weight of Dipropylene gycol is replaced by the same amount of the indene of Example 4.

The substitution of the dipropylene glycol by the indene of Example 4 gives the fragrance surprisingly and desirably a more woody, ambery odour in the topnote and a more woody, creamy in the direction sandalwood odour in the dry-out note. The indene of Example 4 surprisingly adds significant body and boosts the sandalwood notes.

EXAMPLE 6

Perfume compositions, especially suited for men's cologne, cosmetic applications and bar soap, were prepared by mixing the following ingredients:

|   |   | Parts by weight |
|---|---|---|
| A. | Oxambrane (PFW) | 10 |
|   | Santrile (PFW) | 380 |
|   | Isononyl acetate | 600 |
|   | Dipropylene glycol | 10 |
|   |   | 1000 |

B. The formulation above wherein the 10 part by weight of Dipropylene glycol is replaced by the same amount of the indene of Example 4.

The subsitution of the dipropylene glycol by the indene of Example 4 gives the fragrance surprisingly and desirably sweeter and petitgrain, ionone odour nuances in the topnote and adds a rich laudanum odour effect to the bottom of the complex.

We claim:

1. An indene of Formula I:

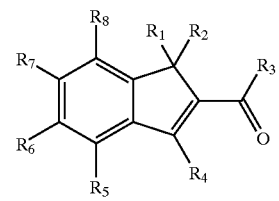

wherein $R_1$, $R_2$ each represent a lower alkyl group and $R_3$, $R_4$, $R_5$, $R_6$, $R_7$ and $R_8$ each represent hydrogen or a lower alkyl group or wherein two substituents chosen from $R_1$, $R_2$, $R_3$, $R_4$, $R_5$, $R_6$, $R_7$ and $R_8$ together may represent a di-, tri- or tetra- or pentamethylene moiety or a lower alkyl-substituted di-, tri- or tetra- or pentamethylene moiety and the remaining substituents represent hydrogen or a lower alkyl group, and wherein the total number of carbon atoms is twenty two or less, with the proviso that $R_1$ and $R_2$ together do not represent a tetramethylene moiety if $R_3$, $R_4$, $R_5$, $R_6$, $R_7$ and $R_8$ all represent hydrogen, and with the proviso that $R_3$ does not represent hydrogen if $R_1$, $R_2$, $R_4$, $R_5$, $R_6$, $R_7$ and $R_8$ all represent a methyl group.

2. The indene according to claim 1, wherein $R_3$ represents an alkyl group of four carbon atoms or less.

3. The indene according to claim 1, wherein $R_3$ is a methyl group.

4. The indene according to claim 1, wherein $R_1$, $R_2$ are selected from methyl and ethyl groups and $R_4$, $R_5$, $R_6$, $R_7$ and $R_8$ each are selected from hydrogen, methyl and ethyl groups with a total number of carbon atoms in $R_1$, $R_2$, $R_3$, $R_4$, $R_5$, $R_6$, $R_7$ and $R_8$ together of eight or less.

5. The indene according to claim 1, wherein $R_1$, $R_2$, and $R_4$ represent each a methyl group.

6. The indene according to claim 1, which is selected from the group of 2-acetyl-1,3,3-trimethylindene, 2-acetyl-1,1,3,6-tetramethylindene, 2-acetyl-1,1,3,5-tetramethylindene and 2-acetyl-1,1,3,5-tetramethylindene.

7. A fragrance composition comprising an indene compound of Formula I,

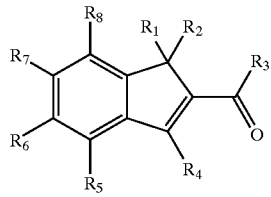

wherein $R_1$ and $R_2$ each represent a lower alkyl group and $R_3$, $R_4$, $R_5$, $R_6$, $R_7$ and $R_8$ each represent hydrogen or a lower alkyl group or wherein two substituents chosen from $R_1$, $R_2$, $R_3$, $R_4$, $R_5$, $R_6$, $R_7$ or $R_8$ together may represent a di-, tri-, tetra- or pentamethylene moiety or a lower alkyl-substituted di-, tri-, tetra- or pentamethylene moiety and the remaining substituents represent hydrogen or a lower alkyl group, and wherein the total number of carbon atoms is twenty two or less.

8. A fragrance composition comprising an indene of Formula I:

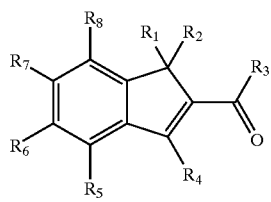

wherein $R_1$, $R_2$ each represent a lower alkyl group and $R_3$, $R_4$, $R_5$, $R_6$, $R_7$ and $R_8$ each represent hydrogen or a lower alkyl group or wherein two substituents chosen from $R_1$, $R_2$, $R_3$, $R_4$, $R_5$, $R_6$, $R_7$ and $R_8$ together may represent a di-, tri- or tetra- or pentamethylene moiety or a lower alkyl-substituted di-, tri- or tetra- or pentamethylene moiety and the remaining substituents represent hydrogen or a lower alkyl group, and wherein the total number of carbon atoms is twenty two or less, with the proviso that $R_1$ and $R_2$ together do not represent a tetramethylene moiety if $R_3$, $R_4$, $R_5$, $R_6$, $R_7$ and $R_8$ all represent hydrogen, and with the proviso that $R_3$ does not represent hydrogen if $R_1$, $R_2$, $R_4$, $R_5$, $R_6$, $R_7$ and $R_8$ all represent a methyl group.

9. The fragrance composition according to claim 8, comprising 0.001–40 wt. % of said indene.

10. A fragrance composition according to claim 8, being in a form chosen from detergents, soaps, fabric softeners, fabric care products, fabric sprays, fabric deodorants, ironing added products, dryer added product, optical whiteners, odour masking products, personal hygiene care products, air fresheners, perfumes, colognes, after shave lotions, bath oils, bath salts, lacquers, brilliantines, pomades, shampoos, creams, deodorants, hand lotions, sun screens, talcs, dusting powders, face powders, masking agents, bleaches, cleaners, dish washing products, scourers, toilet cleaners, carpet cleaners, paints, inks, shoe polish and automobile wax.

11. A method of forming a fragrance composition comprising mixing a natural oil, synthetic oil, alcohol, aldehyde, ketone, ester, lactone, ether, hydrocarbon or nitrile with an idene of Formula I:

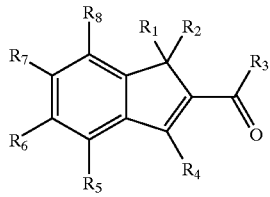

wherein $R_1$, $R_2$ each represent a lower alkyl group and $R_3$, $R_4$, $R_5$, $R_6$, $R_7$ and $R_8$ each represent hydrogen or a lower alkyl group or wherein two substituents chosen from $R_1$, $R_2$, $R_3$, $R_4$, $R_5$, $R_6$, $R_7$ and $R_8$ together may represent a di-, tri- or tetra- or pentamethylene moiety or a lower alkyl-substituted di-, tri- or tetra- or pentamethylene moiety and the remaining substituents represent hydrogen or a lower alkyl group, and wherein the total number of carbon atoms is twenty two or less, with the proviso that $R_1$ and $R_2$ together do not represent a tetramethylene moiety if $R_3$, $R_4$, $R_5$, $R_6$, $R_7$ and $R_8$ all represent hydrogen, and with the proviso that $R_3$ does not represent hydrogen if $R_1$, $R_2$, $R_4$, $R_5$, $R_6$, $R_7$ and $R_8$ all represent a methyl group.

12. A method of enhancing and/or reinforcing the aroma characteristics of natural or synthetic materials comprising mixing natural or synthetic materials with an indene of Formula 1:

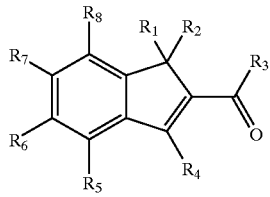

wherein $R_1$, $R_2$ each represent a lower alkyl group and $R_3$, $R_4$, $R_5$, $R_6$, $R_7$ and $R_8$ each represent hydrogen or a lower alkyl group or wherein two substituents chosen from $R_1$, $R_2$, $R_3$, $R_4$, $R_5$, $R_6$, $R_7$ and $R_8$ together may represent a di-, tri- or tetra- or pentamethylene moiety or a lower alkyl-substituted di-, tri- or tetra- or pentamethylene moiety and the remaining substituents represent hydrogen or a lower alkyl group, and wherein the total number of carbon atoms is twenty two or less, with the proviso that $R_1$ and $R_2$ together do not represent a tetramethylene moiety if $R_3$, $R_4$, $R_5$, $R_6$, $R_7$ and $R_8$ all represent hydrogen, and with the proviso that $R_3$ does not represent hydrogen if $R_1$, $R_2$, $R_4$, $R_5$, $R_6$, $R_7$ and $R_8$ all represent a methyl group.

13. A method for producing an indene compound comprising the selective formylation or acylation of an alkene moiety of an indene of Formula II:

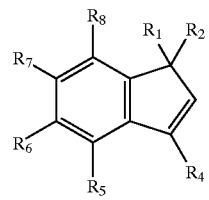

wherein $R_1$, $R_2$ each represent a lower alkyl group and $R_3$, $R_4$, $R_5$, $R_6$, $R_7$ and $R_8$ each represent hydrogen or a lower alkyl group or wherein two substituents chosen from $R_1$, $R_2$, $R_3$, $R_4$, $R_5$, $R_6$, $R_7$ or $R_8$ together may represent a di-, tri-or tetra- or pentamethylene moiety or a lower alkyl-substituted di, tri- or tetra- or pentamethylene moiety and the remaining substituents represent hydrogen or a lower alkyl group, with the proviso the $R_1$ and $R_2$ together do not represent a tetramethylene moiety if $R_3$, $R_4$, $R_5$, $R_6$, $R_7$ and $R_8$ all represent hydrogen, and with the proviso that $R_3$ does not represent hydrogen if $R_1$, $R_2$, $R_4$, $R_5$, $R_6$, $R_7$ and $R_8$ all represent a methyl group.

14. A method for producing an indene compound of Formula I:

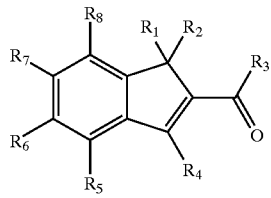

I wherein $R_1$ and $R_2$ each represent a lower alkyl group and $R_3$, $R_4$, $R_5$, $R_6$, $R_7$ and $R_8$ each represent hydrogen or a lower alkyl group or wherein two substituents chosen from $R_1$, $R_2$, $R_3$, $R_4$, $R_5$, $R_6$, $R_7$ or $R_8$ together may represent a di-, tri-, tetra- or pentamethylene moiety or a lower alkyl-substituted di-, tri-, tetra- or pentamethylene moiety and the remaining substituents represent hydrogen or a lower alkyl group, and wherein the total number of carbon atoms is twenty two or less, comprising the conversion under Friedel Crafts acylation conditions of indanes of Formula III:

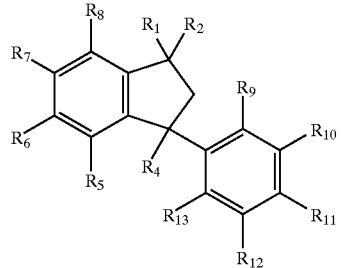

III wherein $R_1$ and $R_2$ each represent a lower alkyl group and $R_3$, $R_4$, $R_5$, $R_6$, $R_7$ and $R_8$ each represent hydrogen or a lower alkyl group or wherein two substituents chosen from $R_1$, $R_2$, $R_3$, $R_4$, $R_5$, $R_6$, $R_7$ or $R_8$ together may represent a di-, tri- or tetra- or pentamethylene moiety or a lower alkyl-substituted di-,tri- or tetra- or pentamethylene moiety and the remaining substituents represent hydrogen or a lower alkyl group and wherein $R_9$, $R_{10}$, $R_{11}$, $R_{12}$, and $R_{13}$ each represent hydrogen or a lower alkyl group or wherein two substituents chosen from $R_1$, $R_2$, $R_3$, $R_4$, $R_5$, $R_6$, $R_7$, $R_8$, $R_9$, $R_{10}$, $R_{11}$, $R_{12}$, or $R_{13}$ or together represent a di-, tri- or tetra- or pentamethylene moiety or a lower alkyl-substituted di-, tri or tetra- or pentamethylene moiety and the remaining substituents represent hydrogen or a lower alkyl group, and wherein the total number of carbon atoms in formula III is fifty or less.

* * * * *

UNITED STATES PATENT AND TRADEMARK OFFICE
CERTIFICATE OF CORRECTION

PATENT NO.    : 6,645,932 B2
DATED         : November 11, 2003
INVENTOR(S)   : Lenselink et al.

Page 1 of 1

It is certified that error appears in the above-identified patent and that said Letters Patent is hereby corrected as shown below:

Column 1,
Line 50, now reads "$R_8$ does not represent hydrogen if $R_1$, $R_2$, $R_4$, $R_5$, $R_6$, $R_{87}$ and" should read -- $R_3$ does not represent hydrogen if $R_1$, $R_2$, $R_4$, $R_5$, $R_6$, $R_{87}$ and --

Column 2,
Line 7, now reads "preferred embodiment $R_8$ is a methyl group. In an alternative" should read -- preferred embodiment $R_3$ is a methyl group. In an alternative --

Signed and Sealed this

Fifteenth Day of June, 2004

JON W. DUDAS
*Acting Director of the United States Patent and Trademark Office*